United States Patent [19]

Fraini et al.

[11] Patent Number: 5,338,453
[45] Date of Patent: Aug. 16, 1994

[54] RECOVERY OF PHENOLS FROM HYDROCARBON MIXTURES

[75] Inventors: Edward A. Fraini, Lake Jackson; George W. Tepera, Sweeny, both of Tex.

[73] Assignee: The Dow Chemical Company, Midland, Mich.

[21] Appl. No.: 920,236

[22] Filed: Jul. 27, 1992

[51] Int. Cl.$^5$ .............................................. B01D 11/04
[52] U.S. Cl. ...................................... 210/634; 210/638
[58] Field of Search .................. 210/634, 638; 568/802, 568/793; 585/800

[56] References Cited

U.S. PATENT DOCUMENTS

| | | | |
|---|---|---|---|
| 2,757,209 | 7/1936 | Joris | 260/621 |
| 3,963,610 | 6/1976 | Hauschulz et al. | 210/636 |
| 4,418,222 | 11/1983 | Honnen | 568/793 |
| 4,973,766 | 11/1990 | Penzo et al. | 568/754 |

*Primary Examiner*—Frank Spear

[57] ABSTRACT

In one aspect this invention includes a method for recovering phenols from a mixture containing hydrocarbons and/or oxygenated hydrocarbons having a boiling point greater than that of the phenol and at least about 1 part per million by weight of at least one phenol comprising, (a) admixing the mixture with sufficient lower molecular weight hydrocarbon solvent to reduce the surface tension of the mixture and (b) contacting the resulting admixture with an aqueous solution of inorganic base such that at least a portion of the phenols are extracted into the aqueous solution. It is found that when recovering phenol from a waste stream which contains in addition to the phenol, a substituted phenol, for example cumyl phenols, extraction with the aqueous phase produces an emulsion. formation of which is reduced or eliminated by use of the lower molecular weight solvent. Reduced emulsion facilitates the unit operation and results in less phenate salt being lost with the emulsion in the organic phase.

22 Claims, No Drawings

5,338,453

RECOVERY OF PHENOLS FROM HYDROCARBON MIXTURES

This invention relates to purification of mixtures, more particularly to purification of mixtures of hydrocarbons and/or oxygenated hydrocarbons containing at least minor amounts of at least one phenol.

Production of phenols from hydrocarbons results in mixtures from which the phenol products are separated by various methods including those taught in such references as U.S. Pat. Nos. 2,757,209 (Madison) and 4,975,766 (Penzo et al.). Typically one or more distillation or other separation processes remove lighter materials from the phenol product and remove the phenol from heavier by-products. Recovering residual phenol from the light and heavy materials has long been of interest. Madison teaches heating a dimethyl phenyl carbinol-containing crude phenol product in the presence of a dimethyl phenyl carbinol dehydration catalyst to form alpha-methyl styrene. After removal of the catalyst, acetone, phenol, unreacted cumene, and the alpha-methyl styrene are then distilled from the reaction mixture in the presence of water. Penzo et al. teach recovery of phenol from a rectification purge containing light materials removed from most of the phenol by distillation: the recovery involves treating the purge with aqueous phenate.

Madison and Penzo et al. deal with recovery of residual phenol from the lighter materials separated from the primary phenol product; however, recovery of phenol from the heavier by-products Left after distillation is also of interest. These heavier products are well known to those skilled in the art and are referred to as bottoms from phenol distillation. The products have been designated K022 (Distillation bottoms tars from the production of phenol/acetone from cumene) on the RCRA (Resource Conservation and Recovery Act) Hazardous Waste designation list and are known to contain phenol and cumylphenols.

It would be desirable to have a way to remove residual phenol from these hydrocarbon materials.

SUMMARY OF THE INVENTION

In one aspect this invention includes a method for recovering phenols from a mixture containing hydrocarbons and/or oxygenated hydrocarbons having a boiling point greater than that of the phenol and at least about 1 percent by weight of at least one phenol comprising, (a) admixing the mixture with sufficient lower molecular weight hydrocarbon solvent to reduce the surface tension of the mixture and (b) contacting the resulting admixture with an aqueous solution of inorganic base such that at least a portion of the phenols are extracted into the aqueous solution.

In the practice of the invention removal of residued phenol(s) is accomplished by an extraction (step 6) which is facilitated by the use of the lower molecular weight solvent (in step A) use of which advantageously reduces or eliminates emulsions which may form between the aqueous organic layers.

DETAILED DESCRIPTION OF THE INVENTION

While this invention is particularly applicable to the recovery of phenol from distillation bottoms obtained in the recovery of phenol from a product mixture obtained from oxidation of hydrocarbons particularly cumene) or from a hydroperoxide e.g. cumene hydroperoxide, it is also applicable to the recovery of any phenol, the phenate of which is soluble in aqueous base from any heavy hydrocarbon and/or oxygenated hydrocarbon mixture therewith. Phenols having phenates soluble in aqueous base (hereinafter soluble phenols) include phenol and alkyl substituted phenols and the like, but (unsubstituted) phenol is preferred in the practice of the invention. Heavy hydrocarbons and oxygenated hydrocarbons include such materials having sufficiently high molecular weights (and boiling points) for the phenol(s) of interest to at least partially distill from the hydrocarbons and/or oxygenated hydrocarbons. The hydrocarbons and/or oxygenated hydrocarbons preferably have aromatic character. Such hydrocarbons include benzene toluene, xylenes and isopropyl benzene, as well as aliphatic and olefinic hydrocarbons in about the $C_5$ to $C_{10}$ range.

The term oxygenated hydrocarbons is used to designate compound having oxygen as well as carbon and hydrogen in their structures and include, carboxylic acids, alcohols and phenols. While oxygenated hydrocarbons in a by-product mixture may not be separated or separately identified, such compounds include those compounds which will form salts with a strong base such as sodium hydroxide. In the practice of the invention in the recovery of unsubstituted phenol from cumyl hydroperoxide or from oxidation of cumene (isopropyl benzene), cumyl phenol and/or oligomers thereof are frequently present and are preferred to De present for practice of the invention. Similarly, in the practice of the invention in the preparation of substituted phenols the corresponding phenolic byproducts of the starting materials are preferably present.

The mixtures contain at least some soluble phenol(s), suitably as little as concentrations in the parts per million (ppm) range, but preferably at least about one percent by weight, more preferably at least 3 percent by weight, most preferably at least 7 percent by weight. While the process is applicable to mixtures containing any proportion of the phenol(s), preferably the mixtures contain less than about 50, more preferably less than about 40, most preferably less than about 15 percent by weight soluble phenol(s).

Any hydrocarbon solvent which lowers the surface tension of the mixture when mixed therewith is suitably used in the practice of the invention. The solvent preferably has a boiling point such that easy recovery is facilitated by distillation, preferably the boiling point is less than 200° C. Suitable solvents include aliphatic and/or olefinic solvents preferably having from about 5 to 10 carbon atoms (linear branched or cyclic) as well as aromatic solvents having boiling points less than that of the materials from which they are subsequently removed, preferably benzene, toluene, xylene, and isopropyl benzene (cumene), more preferably the hydrocarbon used as a starting material for the phenol in a process for making a phenol, most preferably cumene in a process for making unsubstituted phenol.

The mixture is admixed with sufficient solvent to reduce the surface tension of the mixture, preferably to sufficiently reduce the surface tension of the mixture to avoid or reduce formation of emulsions in subsequent contact with aqueous base. Preferably a weight ratio of solvent to mixture is at least about 1:1, more preferably about 1.5:1, most preferably 2:1. While use of additional solvent is effective in the practice of the invention, preferably the weight ratio of solvent to mixture is less than about 4:1, more preferably less than about 3:1, most preferably less than about 2.5:1 because it is unnecessary to use more solvent and requires more separation of solvent from residual mixture after the phenol(s) are removed.

Admixing of the solvent with the mixture preferably occurs before contacting with aqueous base, but can optionally take place thereafter.

Any aqueous solution of base effective in dissolving the phenol(s) of interest is suitably used in the practice of the invention. Preferably, for reasons of separability, the base is inorganic, more preferably a soluble metal hydroxide. Such bases include lithium, potassium, and sodium hydroxides, preferably sodium hydroxide, because of availability.

The aqueous solution of base is suitably in any concentration effective to extract at least a portion of the phenol(s) from the mixture, preferably the concentration is at least about 5 percent, more preferably at least about 10 percent, most preferably at least about 20 percent by weight. The concentration is suitably up to about the saturation concentration of the base in water, but is preferably less than about 50 percent, more preferably less than about 30 percent, most preferably less than about 20 percent by weight. The aqueous solution is preferably used in a mole ratio of at least about 0.5:1, more preferably about 1:1, most preferably about 1.5:1 relative to the phenolic compound content. While the aqueous base solution is optionally used on any effective quantity, it is preferably used in amounts of less than about 2:1, more preferably less than about 1:5, most preferably less than about 1:25 mole ratio based on phenolic compound.

Thorough mixing enhances extraction by base. Mixing is accomplished by means within the state of the art such as with static mixers in a pipe, across a valve, or in a stirred batch vessel. A counter current extractor advantageously enhances the extraction by increasing staging, a term used to define the effect of equilibrium driving forces in a counter current extractor.

While not critical, the temperature of each of these steps is preferably at least about ambient (25°–30° C.) and preferably less than about 200° C. (or the boiling point of the solvent at the pressure used), more preferably less than about 100° C., most preferably less than about 50° C. Any pressure at which the steps occur is suitable but the pressure is preferably at least about atmospheric (100 kPa), and less than about 250 psig (pounds per square inch gauge) (1725 kPag), more preferably less than about 100 psig (690 kPag), most preferably less than about 50 psig (345 kPag).

At higher concentrations (e.g. greater than about 15 weight percent) hydroxide use of higher temperatures within the ranges is advantageous because heat increases solubility of phenate salts.

Reduction or elimination of emulsions of the type observed in the absence of lower molecular weight hydrocarbon solvent is advantageous in carrying out the extraction (unit operation) smoothly, and also has the advantage of improving efficiency of phenolic compound recovery as compared to loss of phenolic compound (as phenate) dissolved in an aqueous phase of an emulsion. When, in the practice of the invention, the aqueous phase separates more cleanly from the organic phase, there is less loss of dissolved phenate in the emulsion: therefore, more phenolic compound recovery. Phenolic compound is recovered by means within the skill in the art such as by lowering the PH of the aqueous phase.

The following examples are given to illustrate but not to limit the invention. Examples (E.X.) of the invention are designated numerically while comparative samples (C.S.) are not examples of the invention and are designated alphabetically. All ratios, percentages, amounts and parts are by weight unless designated otherwise.

COMPARATIVE SAMPLE A

Extraction of Phenol using Aqueous Base Alone

A sample, 25 grams, of a bottoms stream generated by the distillation of recoverable products from a cumene oxidation process is placed in a 250 cc (mL) separatory Funnel with no isopropyl benzene as a co-solvent. Based on the phenol concentration of this sample as determined by G.C. (gas chromatography), sodium hydroxide as a 20 percent solution is added in a 30 percent molar excess amount. The sample is vigorously mixed by shaking. After three minutes, the aqueous phase containing the sodium phenate salt is removed from the separation funnel. The oil phase is sampled and analyzed by Karl Fisher Reagent for water retained to gauge the separation efficiency of the oil/water mix. In this example the oil phase is found to contain 25 weight percent water. The oil phase is allowed to settle completely and is washed with an aliquot of water and then analyzed for phenol. Less than ten percent of the original concentration of phenol remains.

EXAMPLE 1

Use of Isopropyl Benzene to Improve the Separation of Phenol from a Mixture

A sample, 25 grams, of a bottoms stream generated by the distillation of recoverable products from acumene oxidation process is mixed in a 250 mL separatory funnel with 25.0 grams of isopropyl benzene. Based on the phenol concentration of this solution, sodium hydroxide as a 20 percent solution is added in a 30 percent molar excess amount. After three minutes of shaking, the aqueous phase containing the sodium phenate salt is removed From the separation funnel. The oil phase is sampled and analyzed for water retained to gauge the separation efficiency of the oil/water mix. In this example the oil phase is found to contain 1.15 weight percent water. The oil phase is allowed to settle completely and is washed with an aliquot of water and then analyzed for phenol. Less than ten percent the original concentration remains. The phases separate better than in Comparative Sample A: while extraction efficiency is the same within limits of measurement, the settling step requires hours in C.S. A but only two minutes or less in this example of the invention.

EXAMPLE 2

Use of Isopropyl Benzene to Improve the Separation of Phenol from a Mixture

The process of Example 1 is repeated using 50.0 g of isopropyl benzene. The oil phase is found to contain 0.63 weight percent water. The oil phase is allowed to settle completely (less than two minutes) and is washed with an aliquot of water and then analyzed for phenol. Less than ten percent of the original concentration remains. After settling, less aqueous phase remains (as determined by visual observation) in the oil (organic) phase as a colloidal suspension. This aqueous phase contains phenate salts; therefore, its presence in the organic phase reduces the efficiency of the unit operation.

EXAMPLE 3

Use of Isopropyl Benzene to Improve the Separation of Phenol from a Mixture

The process of Example 1 is repeated using 75.0 g isopropyl benzene. The oil phase is found to contain 0.43 weight percent water. The oil phase is allowed to settle completely (less than two minutes) and is washed with an aliquot of water and then analyzed for phenol. Less than ten percent of the original concentration remains. Even less colloidal suspension is noted in the organic phase than is observed in Example 2; thus, the process is more efficient.

EXAMPLE 4

Use of Isopropyl Benzene to Improve the Separation of Phenol from a Mixture

The procedure of Example 1 is repeated using 100.00 g isopropyl benzene. The oil phase is found to contain 0.36 weight percent water. The oil phase is allowed to settle completely (less than two minutes) and is washed with an aliquot of water and then analyzed for phenol. Less than ten percent of the original concentration remains. Still less colloidal suspension than is observed in Example B is noted in Example 4. Thus the process as practiced in Example 4 is even more efficient than in Examples 3, 2, 1 or C.S. A.

What is claimed is:

1. A process for recovering phenols from a mixture containing hydrocarbons and/or oxygenated hydrocarbons having a boiling point greater than that of the phenol and at least about 1 part per million by weight of at least one phenol comprising, (a) admixing the mixture with sufficient lower molecular weight hydrocarbon solvent to reduce the surface tension of the mixture and (b) contacting the resulting admixture with an aqueous solution of inorganic base such that at least a portion of the phenols are extracted into the aqueous solution.

2. The process of claim 1 wherein the solvent is used in a weight ratio to mixture of at least about 1:1.

3. The process of claim 2 wherein the solvent used in a weight ratio to mixture of less than about 4.1.

4. The process of claim 1 wherein the aqueous base is used in a mole ratio to admixture including solvent of at least about 1:1.

5. The process of claim 1 wherein step (a) is preceded by a step (c) forming a phenol from a hydrocarbon hydroperoxide.

6. The process of claim 5 wherein there is additionally a step (d) of distilling at least a portion of the phenol and lower boiling materials from a heavier fraction which is then used as the mixture in step (a).

7. The process of claim 6 where at least one phenol is unsubstituted phenol and at least one hydrocarbon hydroperoxide is cumyl hydroperoxide.

8. The process of claim 1 wherein the lower molecular weight hydrocarbon solvent is one which lowers the surface tens on of the mixture when admixed therewith.

9. The process of claim 8 wherein the lower molecular weight hydrocarbon solvent has a boiling point less than 200° C.

10. The process of claim 9 wherein the lower molecular weight hydrocarbon solvent is an aliphatic and/or olefinic solvent having from about 5 to about 10 carbon atoms.

11. The process of claim 9 wherein the lower molecular weight hydrocarbon solvent is an aromatic solvent.

12. The process of claim 11 wherein the lower molecular weight hydrocarbon solvent is selected from benzene, toluene, xylene and isopropyl benzene.

13. The process of claim 12 wherein the lower molecular weight hydrocarbon solvent is isopropyl benzene.

14. The process of claim 7 wherein the lower molecular weight hydrocarbon solvent is one which lowers the surface tension of the mixture when admixed therewith.

15. The process of claim 14 wherein the lower molecular weight hydrocarbon solvent is an aromatic solvent having a boiling point less than 200° C.

16. The process of claim 15 wherein the lower molecular weight hydrocarbon solvent is selected from benzene, toluene, xylene and isopropyl benzene.

17. The process of claim 16 wherein the lower molecular weight hydrocarbon solvent is isopropyl benzene.

18. The process of claim 17 wherein the aqueous base is used in a mole ratio to admixture including solvent of at least about 1:1.

19. The process of claim 2 wherein the lower molecular weight hydrocarbon solvent is one which lowers the surface tension of the mixture when admixed therewith and has a boiling point of less than 200° C.

20. The process of claim 19 wherein the lower molecular weight hydrocarbon solvent is an aliphatic and/or olefinic solvent having from about 5 to about 10 carbon atoms or an aromatic solvent.

21. The process of claim 19 wherein the lower molecular weight hydrocarbon solvent is selected from benzene, toluene, xylene and isopropyl benzene.

22. The process of claim 21 wherein the phenol is unsubstituted phenol.

* * * * *